United States Patent [19]
Ginnasi et al.

[11] 3,963,586

[45] June 15, 1976

[54] EXTRACTIVE DISTILLATION OF A DIMETHYL CARBONATE FEED WITH WATER

[75] Inventors: Alessandro Ginnasi, San Donato Milanese; Giovanni Passoni, San Giuliano Milanese, both of Italy

[73] Assignee: Snam Progetti S.p.A., San Donato Milanese, Italy

[22] Filed: Oct. 25, 1974

[21] Appl. No.: 518,192

[30] Foreign Application Priority Data
Oct. 26, 1973 Italy .................................. 30596/73

[52] U.S. Cl. .................................. 203/96; 260/463
[51] Int. Cl.² .......................... B01D 3/34; B01D 3/38
[58] Field of Search .............................. 203/95–97, 203/39; 260/463

[56] References Cited
UNITED STATES PATENTS

| | | | |
|---|---|---|---|
| 2,517,965 | 8/1950 | Bohl | 260/463 |
| 2,687,425 | 8/1954 | Douthitt | 260/463 |
| 2,787,631 | 4/1957 | Stevens | 260/463 |

*Primary Examiner*—Bernard Nozick
*Assistant Examiner*—Frank Sever
*Attorney, Agent, or Firm*—Ralph M. Watson

[57] ABSTRACT

Dimethyl carbonate is separated from a mixture thereof with methyl alcohol and water through an extractive distillation process wherein water is utilized as the solvent.

1 Claim, No Drawings

EXTRACTIVE DISTILLATION OF A DIMETHYL CARBONATE FEED WITH WATER

The present invention relates to a process for the purification of the esters of carbonic acid.

More particularly the present invention relates to a process for the purification of dimethyl carbonate.

As known (see Italian patent application No. 21468 A/70 and the corresponding U.S. Pat. No. 3,846,468) the esters of carbonic acid having the general formula

wherein R is hydrocarbon radical of alkyl, aryl or cycloalkyl type are produced by reaction of an alcohol ROH, wherein R has the aforesaid meaning, with $CO_2$ and $O_2$ in the presence of a catalyst constituted by a compound of a metal belonging to the following groups of the periodic system: IB, IIB and VIII.

In the particular case of dimethyl carbonate the starting alcohol is methyl alcohol.

We shall make reference in the following description to dimethyl carbonate even though the process of the present invention is utilizable for the purification of any ester of carbonic acid. The reactions of formation of dimethyl carbonate are the following:

Phase 1 (oxidation)

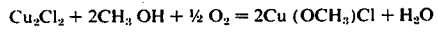

Phase 2 (reduction)

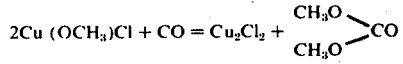

The catalyst in general is dissolved in pyridine.

The oxidation reaction is carried out in the presence of an excess of methyl alcohol.

For this reason in the final product one will find $Cu_2Cl_2$, dimethyl carbonate, water and methyl alcohol and pyridine. $Cu_2Cl_2$ and pyridine are removed from the mixture by means known to those skilled in the art.

The separation of dimethyl carbonate from water and methyl alcohol is, however, too complicated for a simple rectification because of the formation of azeotropes which make difficult its separation to the desired specification.

In the case of other esters obviously the separation is that which involves such esters, the alcohols from which they have been obtained and water. It has been surprisingly found, and this constitutes the subject of the present invention, that it is possible to separate dimethyl carbonate from water and methyl alcohol by using an extractive distillation using water as solvent.

The process of the present invention consists in feeding to the intermediate zone of an extractive distillation column a mixture constituted by methyl alcohol, water, dimethyl carbonate. To the top or in proximity to the top we feed water which is used as solvent.

The water/feed ratio is determined by the solubility of dimethyl carbonate on the top plate and is at least 10 times the reflux rate to the column.

The highest limit is imposed only by economical considerations.

The overhead product is constituted by dimethyl carbonate and water which separate into two phases on cooling; the organic phase contains dimethyl carbonate; the aqueous phase is recycled to the column.

The bottom product constituted by methyl alcohol and water is subjected to rectification in order to separate methyl alcohol from water: water is recycled to the extractive distillation and methyl alcohol to the reaction.

We shall now give an illustrative example of the invention without thereby restricting the same.

EXAMPLE

To a column, provided with perforated plates, of the Oldershow type having a diameter of 1" and 25 plates we fed onto the 15th plate 100g/h of a solution constituted by dimethyl carbonate - methyl alcohol - water at the ratio (48/48/4) by weight obtained by synthesis.

To the 25th plate we fed water as extractive solvent at the rate of 950 g/h.

The conditions of the column were:
Pressure: 1 atmosphere
Overhead reflux ratio: 1
Reboiler temperature: 99°C
Overhead temperature: 79.5°C
Temperature of the entering feed: 69.0°C (vapour phase)
Temperature of the extraction water: 76.0°C.

The overhead product was separated by decantation obtaining two streams: an organic stream and an aqueous stream.

The rate of the overhead organic product was 50 g/h and its composition was 0.3% methyl alcohol, 97% dimethyl carbonate and 2.7% water while the rate of the aqueous overhead product was 7 g/h and its composition was 1.2% methyl alcohol, 11.8% dimethyl carbonate and 87% water.

The bottom product had as composition: ~5% methyl alcohol, <0.05 dimethyl carbonate and 95% water.

What we claim is:

1. The process of separating dimethyl carbonate from a mixture thereof with methyl alcohol and water through an extractive distillation comprising the steps of feeding said mixture to an intermediate zone of an extractive distillation column, feeding solvent water in an amount equal to at least 10 times the column reflux rate to said column at a point in proximity to its top, withdrawing a stream of methyl alcohol and water from the bottom of said column, withdrawing from the top of said column a stream having an organic phase containing dimethylcarbonate and an aqueous phase, and separating said organic phase from the aqueous phase.

* * * * *